(12) United States Patent
Albertorio et al.

(10) Patent No.: US 8,920,497 B2
(45) Date of Patent: Dec. 30, 2014

(54) METHOD AND INSTRUMENTATION FOR ACETABULAR LABRUM RECONSTRUCTION

(75) Inventors: Ricardo Albertorio, Naples, FL (US); Arley Perez, III, Bonita Springs, FL (US); Benjamin G. Domb, Chicago, IL (US); Robert K. Sluss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 13/343,365

(22) Filed: Jan. 4, 2012

(65) Prior Publication Data
US 2012/0185058 A1  Jul. 19, 2012

Related U.S. Application Data

(60) Provisional application No. 61/429,482, filed on Jan. 4, 2011.

(51) Int. Cl.
| | |
|---|---|
| *A61F 2/08* | (2006.01) |
| *A61F 2/30* | (2006.01) |
| *A61B 19/00* | (2006.01) |
| *A61F 2/34* | (2006.01) |

(52) U.S. Cl.
CPC ....... *A61F 2/30756* (2013.01); *A61B 2019/461* (2013.01); *A61F 2310/00371* (2013.01); *A61F 2002/30731* (2013.01); *A61F 2/34* (2013.01)
USPC ..................................... 623/14.12

(58) Field of Classification Search
USPC ............................ 623/14.12, 22.21
See application file for complete search history.

(56) References Cited

U.S. PATENT DOCUMENTS

| | | | | |
|---|---|---|---|---|
| 5,581,901 | A  * | 12/1996 | Takahashi .................... 33/756 |
| 7,879,105 | B2 * | 2/2011 | Schmieding et al. ...... 623/19.11 |
| 2005/0267584 | A1* | 12/2005 | Burdulis et al. ........... 623/20.19 |
| 2008/0208253 | A1* | 8/2008 | Dreyfuss et al. ............. 606/232 |
| 2011/0093073 | A1* | 4/2011 | Gatt et al. ................. 623/14.12 |
| 2012/0283840 | A1* | 11/2012 | Frederick et al. ......... 623/22.32 |

* cited by examiner

*Primary Examiner* — Randy Shay
(74) *Attorney, Agent, or Firm* — Dickstein Shapiro LLP

(57) ABSTRACT

Methods and instruments for repairing a damaged acetabular labrum. The arc length of a portion of an acetabular rim proximal to the damaged (torn or broken) region of the acetabular labrum is measured, and a graft, such as a meniscal allograft or a gracilis autograft, is trimmed according to the measurement and secured in the damaged region of the acetabular labrum as a replacement. Various instruments, such as a wheel mounted on an arm, a measuring member with spaced tines, or a hollow arm with a graduated wire, can be used to measure the arc length of the damaged region of the acetabular labrum.

7 Claims, 8 Drawing Sheets

METHOD AND INSTRUMENTATION FOR ACETABULAR LABRUM RECONSTRUCTION

This application claims the benefit of U.S. Provisional Application No. 61/429,482, filed on Jan. 4, 2011.

FIELD OF THE INVENTION

This invention relates generally to the field of surgery, and more specifically to a surgical method for repairing the acetabular labrum. The invention also relates to a method of preparing a graft, such as an allograft meniscus, for repairing a damaged acetabular labrum.

BACKGROUND OF THE INVENTION

Injuries to the acetabular labrum, a ring of cartilage that surrounds the actebulum, or hip joint, are common. Acetabular labrum injuries may be caused by femoral impingement, such as cam or pincer lesions, hip disclocation, or dysplasia.

When the acetabular labrum is damaged beyond repair, surgeons commonly practice labral resection. More recently, some surgeons have attempted to reconstruct the damaged acetabular labrum with substitute tissue. Prior attempts at labral reconstruction have utilized techniques and materials similar to those which are known for use in ACL repair. However, the ACL has neither the triangular cross-sectional shape nor the mechanical properties of the acetabular labrum, which is formed of cartilage. For this and other reasons, prior attempts at reconstructing the acetabular labrum have not yielded satisfactory results.

SUMMARY OF THE INVENTION

The present invention overcomes the above-mentioned deficiencies of the prior art by providing a method for repairing the acetabular labrum using an allograft meniscus. Specifically, the present invention involves measuring an arc length of a portion of an acetabular rim proximal to the damaged (torn or broken) region of the acetabular labrum and placing a graft in the damaged region of the acetabular labrum. A measuring instrument, such as a wheel mounted on an arm can be used to measure the arc length of the damaged region of the acetabular labrum. The wheel is moved across the surface of the acetabular rim from one end of the damaged region to the opposite end, and the number of rotations of the wheel are counted to determine the arc length of the portion of an acetabular rim proximal to the damaged region of the acetabular labrum.

Another instrument that can be used to determine the arc length of the portion of an acetabular rim proximal to the damaged region of the acetabular labrum includes an arm with first and second tines spaced a known distance apart. The measurement is taken by placing the first tine of the measuring member on a surface of the acetabular rim adjacent to a first end of the damaged region of the acetabular labrum, placing the second tine of the measuring member on a surface of the acetabular rim, moving the measuring member along the acetabular rim to a surface of the acetabular rim adjacent to a second end of the damaged region of the acetabular labrum such that the start of each movement corresponds with the end of the previous movement (the movement involving rotation, translation, or a combination of the two), counting the number of movements required to reach the surface of the acetabular rim adjacent to the second end of the damaged region of the acetabular labrum, and determining, from the count, the arc length of the portion of an acetabular rim proximal to the damaged region of the acetabular labrum.

Yet another instrument that can be used to determine the arc length of the portion of an acetabular rim proximal to the damaged region of the acetabular labrum includes a hollow arm, a graduated wire at least partially contained within the hollow arm, and an anchor attached to one end of the graduated wire. The measurement with this instrument is accomplished by placing the anchor on or in the acetabular rim adjacent to the first end of the damaged region of the acetabular labrum, moving the hollow arm to a surface of the acetabular rim adjacent to the second end of the damaged region of the acetabular labrum, and determining the arc length of the portion of the acetabular rim adjacent to the damaged region of the acetabular labrum.

Once the arc length of the portion of an acetabular rim proximal to the damaged region of the acetabular labrum has been measured, the allograft meniscus is prepared, a plurality of anchor holes are drilled in the acetabular rim, and the allograft meniscus is secured to acetabular rim, preferably using knotless suture anchors (to anchor suture stitched through the allograft meniscus.

BRIEF DESCRIPTION OF THE DRAWINGS

Other features and advantages of the present invention will become apparent when the following description is read in conjunction with the accompanying drawings, in which.

DETAILED DESCRIPTION OF THE INVENTION

In one embodiment, the invention relates to a method of repairing a damaged acetabular labrum using a graft such as an allograft meniscus. In another embodiment, the invention relates to a method of preparing a graft, such as an allograft meniscus. The graft prepared by this method can be used in a variety of surgical and non-surgical techniques, including, but not limited to, the disclosed method of repairing a damaged acetabular labrum.

Reference is now made to the accompanying drawings, which are not to scale, and in which like numbers represent like elements. Note that while the drawings explain various aspects of the invention with respect to measuring portions of the acetabulum and repairing the acetabular labrum with an allograft meniscus, it is to be understood that the methods described may also be applied to other bones and to other types of grafts.

Figure 1:
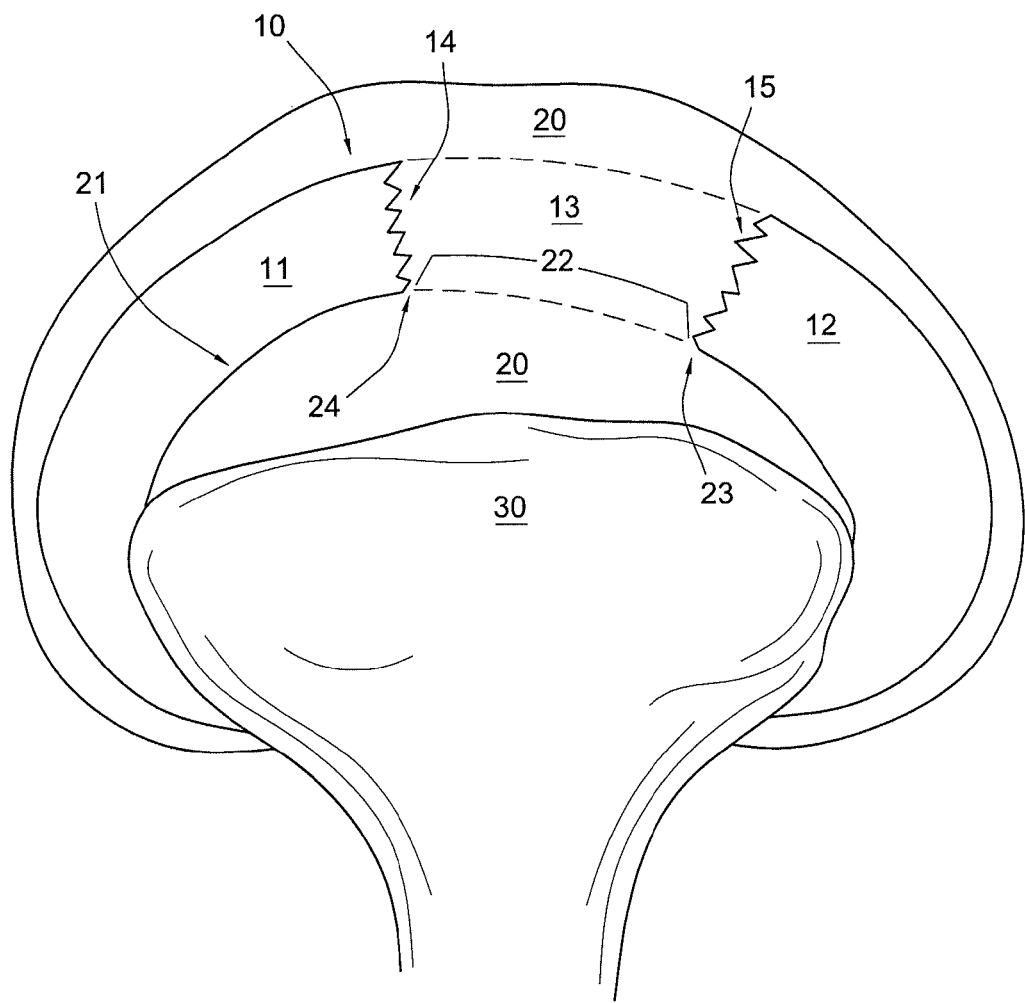
FIG. 1 depicts a damaged acetabular labrum.

FIG. 1 shows acetabular 20, which comprises acetabular rim 21. The acetabular 20 is a socket, in which the ball end of femur 30 is received. Native acetabular labrum 10 contains a first region 11 and second region 12, both of which contact damaged region 13. Damaged region 13 is torn or broken, and is therefore represented by dashed lines. The acetabular rim 21 includes a surface 23 adjacent to a first end of the damaged acetabular labrum 13, and another surface 24 adjacent to a second end of the damaged acetabular labrum 13. The acetabular rim 20 also includes a portion 22 that is adjacent to the damaged region 13 of the acetabular labrum 10.

A native graft, such as a native allograft meniscus, may not have the correct arc length and curvature for use in repairing a damaged acetabular labrum. Thus, in accordance with the present invention, the native graft is prepared by measuring the desired arc length of the acetabular rim, a curved bone, and then trimming the native graft to the proper arc length and curvature. More specifically, the arc length and curvature of the graft is formed to be substantially similar to the arc length and curvature of a portion 22 of the acetabular rim 20 that is adjacent to the damaged region 13 of the acetabular labrum 10.

Figure 2:
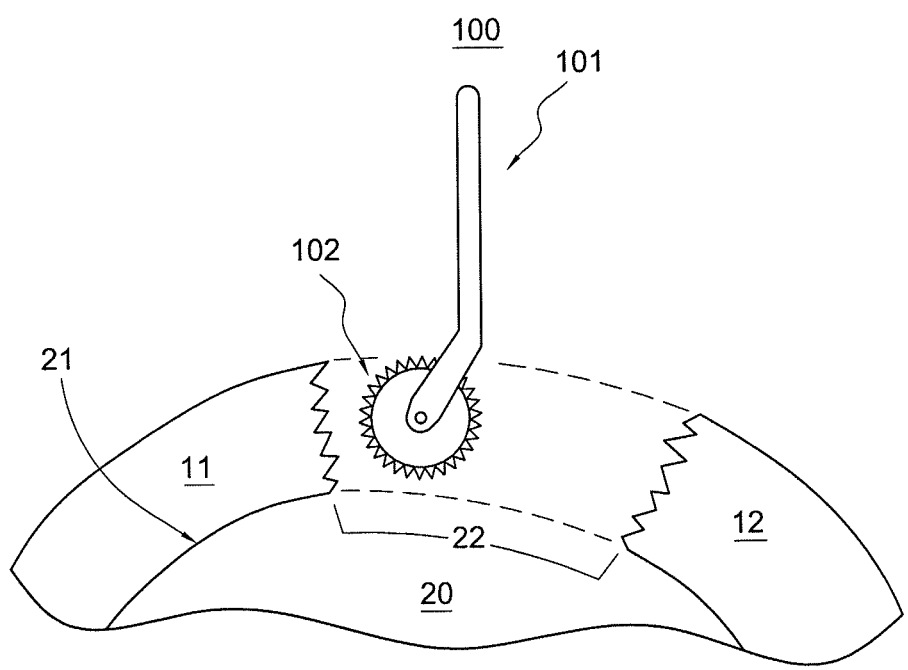
FIG. 2 depicts an instrument for measuring an arc length of a portion of bone.

FIG. 2 shows a pinwheel instrument 100 for measuring the arc length of a portion of a bone with a curvature, such as the acetabular rim. Pinwheel instrument 100 comprises arm 101 and wheel 102 attached thereto. Wheel 101 has a known circumference, such that the distance traveled by the wheel 102 can be determined by counting the number of rotations of the wheel 102.

In use, the wheel 102 of pinwheel instrument 100 is contacted with a surface of acetabular rim 21 adjacent to a first end of the damaged acetabular labrum 13. The wheel 102 is then moved across the acetabular rim until it reaches a surface of the acetabular rim 21 adjacent to the second end of the damaged region of the acetabular labrum 13. The wheel 102 rotates as it moves across the surface of the portion 22 of the acetabular rim 20 adjacent to the damaged tissue. By counting the number of rotations or partial rotations of wheel 102, the arc length of the portion of the acetabular rim 22 adjacent to the damaged region 13 of acetabular labrum 10 can be determined.

Figure 3:
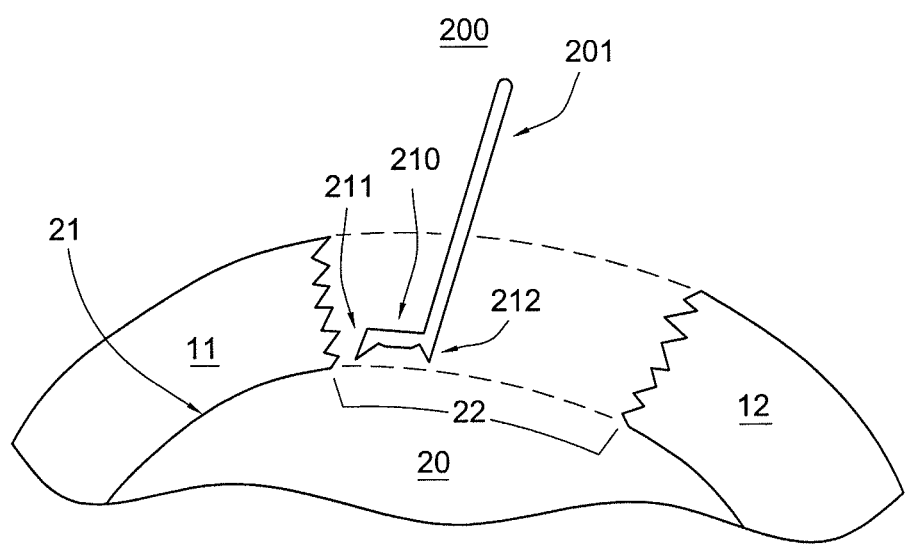
FIG. 3 depicts an instrument for measuring an arc length of a portion of bone.

FIG. 3 shows fork-like instrument 200 for measuring the arc length of a portion of a bone with a curvature. Fork-like instrument 200 comprises arm 201 and measuring member 210 attached thereto. Measuring member 210 includes two tines, 211 and 212. The two tines 211 and 212 are spaced a known distance apart.

In use, a first tine, which may be tine 211 or 212, is contacted with a surface of acetabular rim 21 adjacent to a first end of the damaged acetabular labrum 13. The second tine is then placed on a surface of the acetabular rim 20. The measuring member is then moved along the acetabular rim 21 in steps, such that the start of each movement corresponds with the end of the previous movement. Each movement may be, for example, rotational or translational. The number of movements required to reach the surface of the portion 22 of the acetabular rim 20 adjacent to the second end of the damaged region 13 of the acetabular labrum 10 is counted, and the arc length of the portion 22 of acetabulum rim 20 adjacent to the damaged region 13 of the acetabular labrum 10 is determined.

Figure 4A:
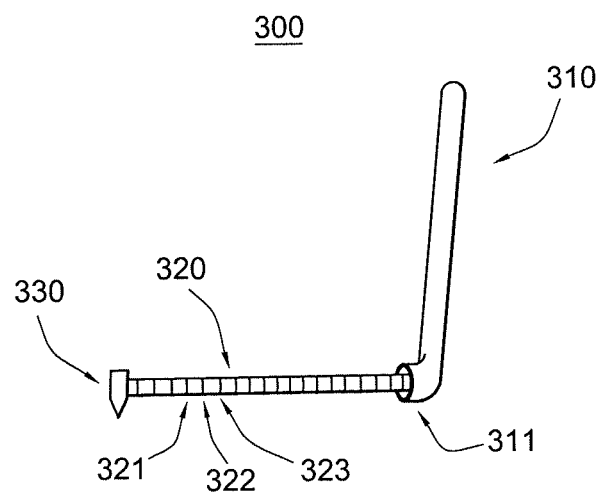
FIG. 4a depicts an instrument for measuring an arc length of a portion of bone.

FIG. 4a shows another measuring instrument 300 for measuring the arc length of a portion of a bone with a curvature. Measuring instrument 300 includes hollow arm 310 with opening 311. Graduated wire 320, which may be made of nitinol, is at least partially contained within hollow arm 310, and can extend out of hollow arm 310 through hole 311. Graduated wire 320 includes graduated markings 321, 322, and 323. Anchor 330 is attached to one end of graduated wire 320.

Figure 4B:
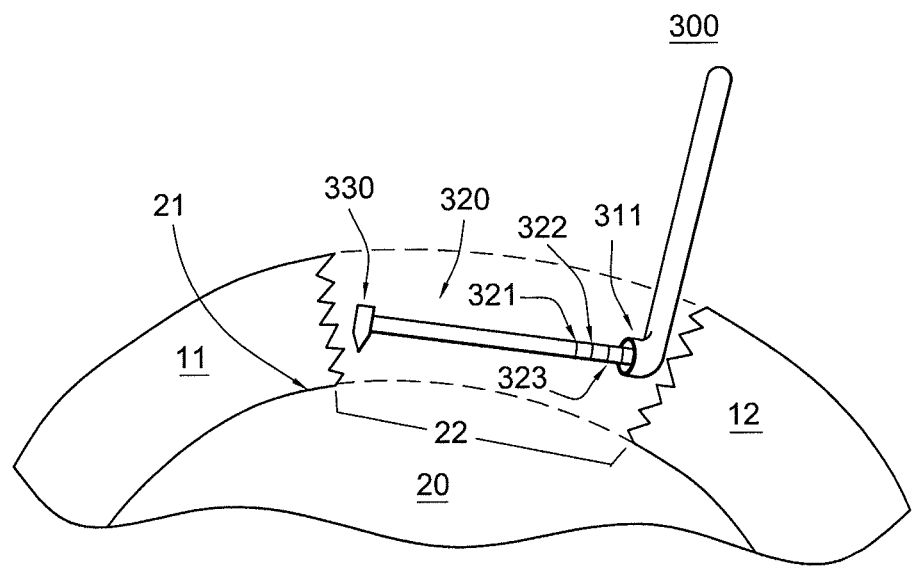
FIG. 4b depicts the instrument of FIG. 4a in use.

FIG. 4b shows measuring instrument 300 in use. In use, anchor 330 is placed in or on a surface of acetabular rim 21 adjacent to a first end of the damaged region of the acetabular labrum. The hollow arm is then moved to a surface of the acetabular rim adjacent to the second end of the damaged acetabular labrum 13, thereby allowing graduated wire 320 to extend out of opening 311. The arc length of the surface of the portion 22 of acetabulum rim 20 adjacent to the damaged region 13 of acetabular labrum 10 may then be determined, for example, by reading graduated markings 321, 322, and 323, or by counting the number of graduated markings 321, 322, and 323 between anchor 330 and hollow arm 310.

Once the arc length of the portion of bone, such as the portion of the acetabulum 22 adjacent to the damaged region 13 of the acetabular labrum 10, is measured, the native graft, which may be a native allograft meniscus or a gracilis autograft, can be trimmed to the appropriate size.

Figure 5A:
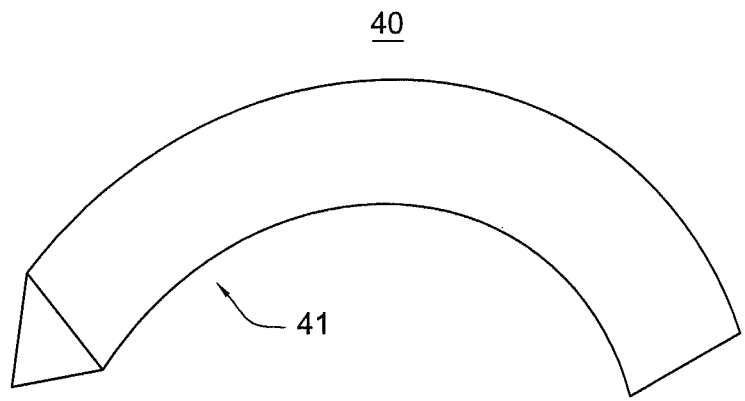
FIG. 5a depicts a native allograft meniscus.

FIG. 5a shows native allograft meniscus 40, having surface 41. Surface 41 has an arc length and curvature that are not substantially similar to the arc length and curvature of the portion 22 of the acetablum 20 adjacent to the damaged region 13 of the acetabular labrum 10 (FIGS. 1-4).

Figure 5B:
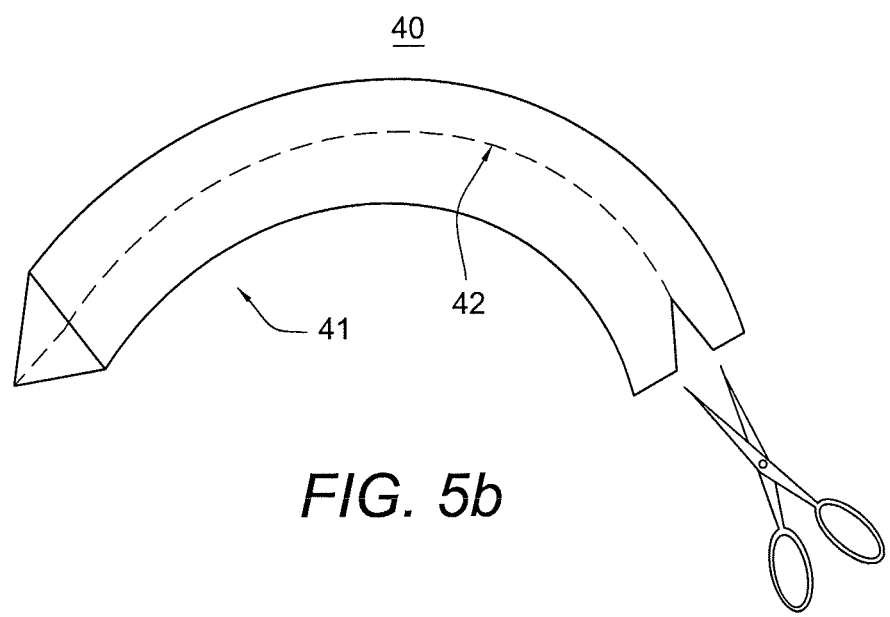
FIG. 5b depicts the native allograft meniscus of FIG. 5a being trimmed.

FIG. 5b shows curve 42 (dashed line), which has an arc length and curvature that are substantially similar to the arc length and curvature of the portion of the acetablum 22 adjacent to the damaged portion of the acetabular labrum 13 (FIGS. 1-4). Cutting implement 400, which may be scissors, a scalpel, a knife, or any other appropriate cutting instrument, is used to trim native allograft meniscus 40 along curve 42.

Figure 6A:
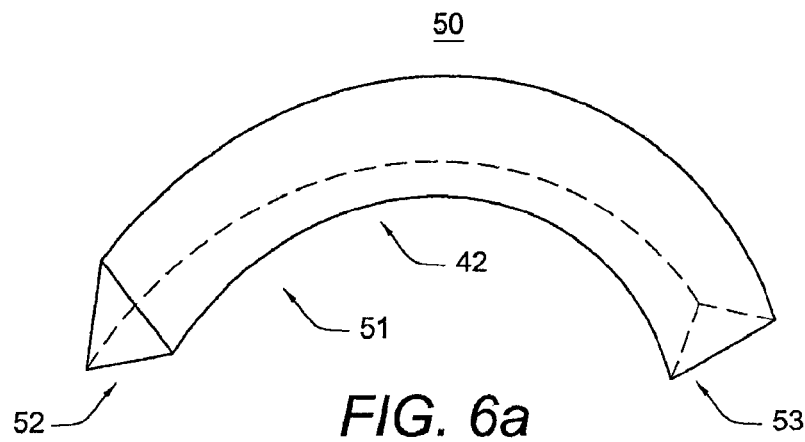
FIGS. 6a-6c depict a trimmed allograft meniscus.

FIG. 6 shows the trimmed allograft meniscus 50, which has a triangular profile in cross-section. As shown in FIG. 6a, where dashed lines represent surfaces that are not visible, the trimmed allograft meniscus 50 has a triangular profile with a first base 52 and second base 53. Surface 51 features curve 42, which has an arc length and curvature that are substantially similar to the arc length and curvature of the portion 22 of the acetabulum 20 adjacent to the damaged region 13 of the acetabular labrum 10 (FIGS. 1-4).

Figure 6B:
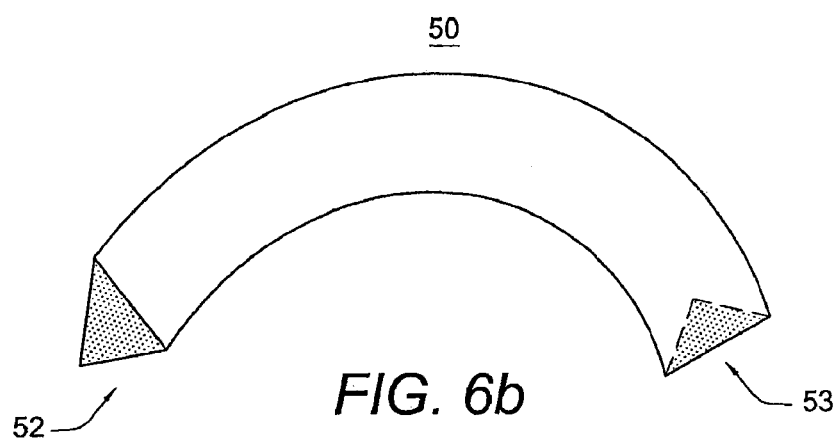

FIG. 6b depicts the first base 52 and second base 53 of trimmed allograft meniscus 50, which have been colored with a surgical marker. The surgical marker may be any surgical marker, such as dyes, pigments, etc., known in the art that allows the surgeon to visualize the first base 52 and second base 53 during surgery, such as arthroscopic surgery.

Figure 6C:
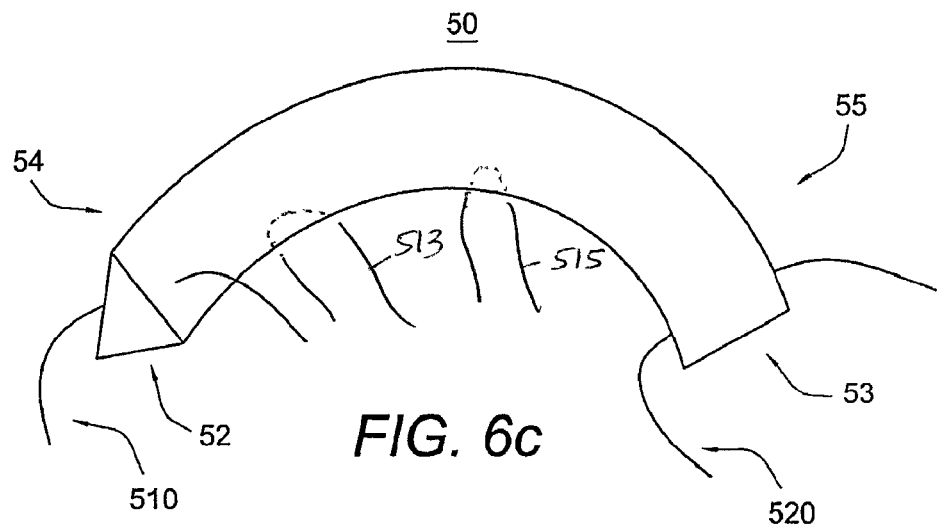

FIG. 6c depicts trimmed allograft meniscus 50, which has a first end 54 and a second end 55. A first tag suture 510 is threaded through the first end 54 of the trimmed allograft meniscus 50, and a second tag suture 520 is threaded through the second end 55 of trimmed allograft meniscus 50. The tag sutures may be made of any known suture material in the art. Tag sutures 510 and 520 may be used by a surgeon to manipulate the graft and introduce it into a desired location.

Figure 7:
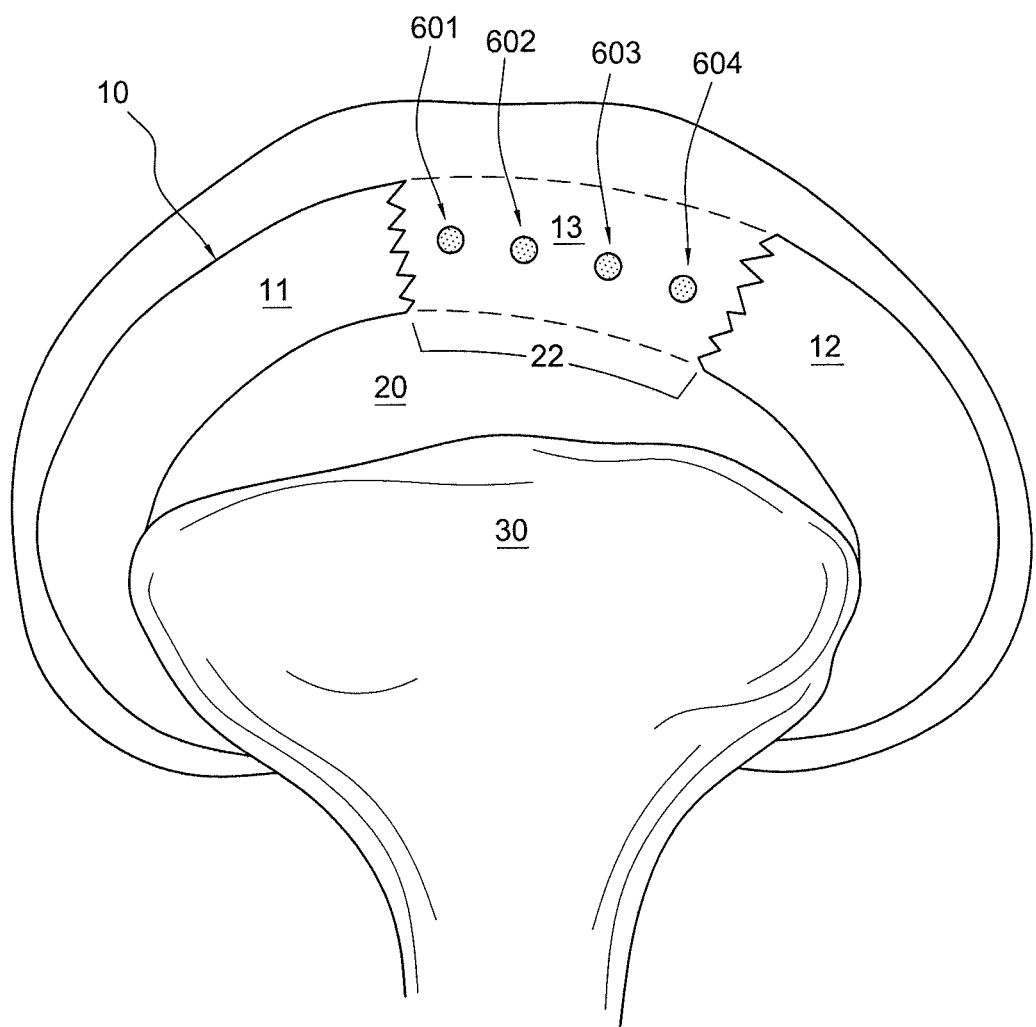
FIG. 7 depicts a damaged acetabular labrum with anchor holes drilled in the acetabular rim.

FIG. 7 depicts acetabulum 20, femur 30, and acetabular labrum 10, which includes first region 11, second region 12, and damaged region 13. Distal anchor holes 601 and 604, and middle anchor holes 602 and 603, are drilled into a portion 22 of acetabulum 20 adjacent to damaged region 13 of acetabular labrum 10. Distal anchor holes 601 and 604, and middle anchor holes, 602 and 603 may be drilled by any means known in the art for drilling holes into bone.

After distal anchor holes 601 and 604, and middle anchor holes, 602 and 603 are drilled, the trimmed allograft meniscus 50 may be introduced. First end 54 and second end 55 of trimmed allograft meniscus 50 are anchored to distal holes 601 and 604 with anchors 701 and 704, respectively, shown schematically in FIG. 8. Any type of anchor known in the art may be used. If knotless anchors, such as those described in U.S. Pat. No. 7,329,272 and US Patent Application Publication No. 2008/0208253, which are hereby incorporated by reference, are used, then the suture bulk may be reduced and no knots that might damage cartilage are present.

Trimmed allograft meniscus 50 is anchored to middle anchor holes 602 and 603 by passing a suture 513, 515 through the first base 52 or second base 53. Any known suture passing instrument, such as an Arthrex Suture Lasso or Penetrator, may be used for this purpose. The suture 513, 515 may then be stitched and anchored to middle hole 602 or 603 using a suture anchor. When a basal stitch is used, the triangular cross-section of the allograft meniscus is maintained, and no suture contacts the femoral cartilage.

Although FIG. 7 shows two middle anchor holes 602 and 603, the number of middle anchor holes may vary depending on the arc length of the allograft meniscus. Most acetabular labrum repairs will be accomplished by using two to four middle anchor holes and two distal anchor holes, for a total of four to six anchor holes. However, some surgeries may require fewer anchor holes, and others may require more. If no middle anchor holes are required, then they may be omitted. If more than two, or more than four, middle anchor holes are required, then the methods described above may be used to anchor the trimmed allograft meniscus 50 to each anchor hole.

Figure 8:
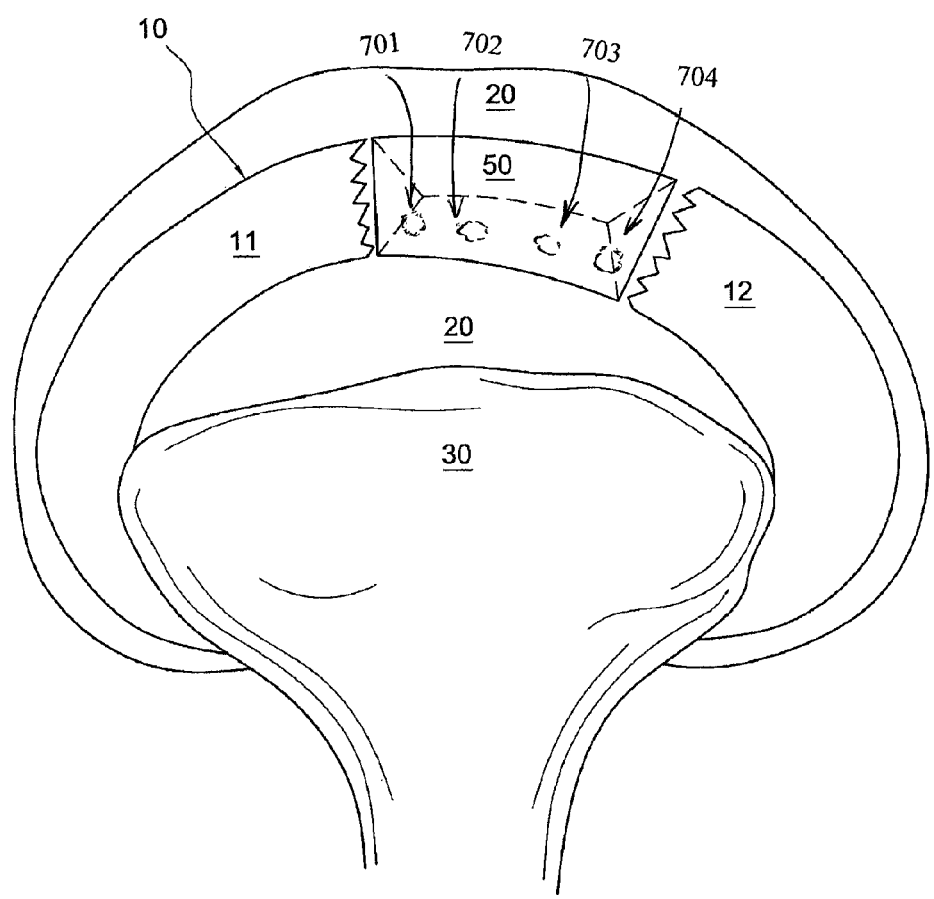
FIG. 8 depicts a repaired acetabular labrum.

FIG. 8 depicts a repaired acetabular labrum 10. Trimmed allograft 50, wherein dashed lines are used to show the triangular profile, has been anchored in place adjacent to a first region 11 and second region 12 of acetabular labrum 10.

While various embodiments of the invention have been described in detail, it should be readily understood that the invention is not limited to the disclosed embodiments. For example, the methods described herein can be used with a gracilis autograft instead of an allograft meniscus, and the methods can be used more generally to prepare any type of graft for implantation, and to measure the arc length of any bone with a curvature. Thus, various modifications to the disclosed embodiments, including variations, alterations, substitutions, or equivalent arrangements not heretofore described may be made without departing from the spirit and scope of the invention.

What is claimed is:

1. A method of repairing a damaged region of a native acetabular labrum, comprising:
    measuring an arc length of an arc of a portion of an acetabular rim proximal to the damaged region of the native acetabular labrum, the native acetabular labrum having a triangular cross-section, wherein the step of measuring the arc length further comprises measuring with an arthroscopic measuring instrument, the arthroscopic measuring instrument comprising a hollow arm and a graduated wire at least partially contained within the hollow arm;
    trimming a native allograft meniscus with a cutting instrument along a curve of the native allograft meniscus to obtain a trimmed graft with a surface having an arc length and curvature substantially similar to the length and curvature of the portion of the acetabular rim, the trimmed graft replicating the triangular cross-section of the native acetabular labrum, the trimmed graft having a first end with a first base and a second end with a second base, the first end and the second end having a triangular cross-section;
    coloring at least one of the first base and second base with a surgical marker to allow visualization of the at least one of the first base and second base during surgery;
    placing sutures through the first end and the second end; and
    placing the trimmed graft in the damaged region of the acetabular labrum by manipulating the sutures at the first and second ends, and securing the trimmed graft in the damaged region as a replacement by attaching the trimmed graft to the acetabular rim with one or more suture anchors,
    wherein the step of securing the trimmed graft in the damaged region of the acetabular labrum further comprises stitching additional sutures through the trimmed graft to form a stitch and subsequently anchoring each of the additional sutures in a respective hole in the acetabular rim using a suture anchor.

2. The method of claim 1 wherein the damaged region of the acetabular labrum is selected from a torn region and a broken region.

3. The method of claim 1, wherein the instrument further comprises an anchor attached to one end of the graduated wire.

4. The method of claim 3, wherein the measuring step further comprises:
    placing the anchor on or in the acetabular rim adjacent to a first end of the damaged region of the acetabular labrum;
    moving the hollow arm to a surface of the acetabular rim adjacent to a second end of the damaged region of the acetabular labrum; and
    determining the length of the arc of the portion of the acetabular rim adjacent to the damaged region of the acetabular labrum.

5. The method of claim 1, further comprising a step of forming one or more anchor holes in the acetabular rim.

6. The method of claim 5, wherein the step of forming one or more anchor holes comprises drilling four, five or six anchor holes in the acetabular rim.

7. The method of claim 1, wherein the suture anchors are knotless suture anchors.

* * * * *